(12) United States Patent
Chen et al.

(10) Patent No.: US 9,751,889 B2
(45) Date of Patent: Sep. 5, 2017

(54) CRYSTALLINE FORM I OF IBRUTINIB

(71) Applicants: CRYSTAL PHARMATECH INC., North Brunswick, NJ (US); SUZHOU PENGXU PHARMATECH CO., LTD., Suzhou (CN)

(72) Inventors: Minhua Chen, Scotch Plains, NJ (US); Yanfeng Zhang, Suzhou (CN); Chaohui Yang, Suzhou (CN); Xiaoyu Zhang, Suzhou (CN); Peng Wang, Forest Hills, NY (US); Pixu Li, Suzhou (CN); Fei Lu, Suzhou (CN); Heng Ge, Suzhou (CN)

(73) Assignees: Crystal Pharmatech Inc., North Brunswick, NJ (US); Suzhou Pengxu Pharmatech Co., Ltd., Suzhou (CN)

( * ) Notice: Subject to any disclaimer, the term of this patent is extended or adjusted under 35 U.S.C. 154(b) by 0 days.

(21) Appl. No.: 15/100,247

(22) PCT Filed: Nov. 26, 2014

(86) PCT No.: PCT/US2014/067586
§ 371 (c)(1),
(2) Date: May 27, 2016

(87) PCT Pub. No.: WO2015/081180
PCT Pub. Date: Jun. 4, 2015

(65) Prior Publication Data
US 2017/0002009 A1    Jan. 5, 2017

(30) Foreign Application Priority Data

Nov. 27, 2013  (CN) .......................... 2013 1 0616065
Oct. 14, 2014   (CN) .......................... 2014 1 0542609

(51) Int. Cl.
| | |
|---|---|
| *A01N 43/90* | (2006.01) |
| *A61K 31/519* | (2006.01) |
| *C07D 487/00* | (2006.01) |
| *C07D 487/04* | (2006.01) |

(52) U.S. Cl.
CPC .......... *C07D 487/04* (2013.01); *A61K 31/519* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 9,296,753 B2 * | 3/2016 | Smyth | ................ C07D 487/04 |
| 9,540,382 B2 * | 1/2017 | Purro | ................. C07D 487/04 |
| 2007/0219195 A1 | 9/2007 | Goldstein et al. | |
| 2012/0077832 A1 | 3/2012 | Witowski et al. | |
| 2013/0005745 A1 | 1/2013 | Honigberg et al. | |

FOREIGN PATENT DOCUMENTS

| | | |
|---|---|---|
| CN | 103121999 A | 5/2013 |
| WO | 2013155347 A1 | 10/2013 |
| WO | 2013157021 A1 | 10/2013 |

* cited by examiner

*Primary Examiner* — Jeffrey H Murray
(74) *Attorney, Agent, or Firm* — VLP Law Group LLP; Kent H. Cheng

(57) ABSTRACT

Crystalline Form I of ibrutinib, processes for its preparation, pharmaceutical compositions comprising the new Form, and use of Form I of ibrutinib for treating or delaying diseases or disorders related to activity of Bruton's tyrosine kinase (BTK) proteins are disclosed. The novel Form was characterized by X-ray powder diffraction, differential scanning calorimetry, and other techniques. It can be readily prepared and is suitable for use in the preparation of solid dosage forms.

19 Claims, 3 Drawing Sheets

CRYSTALLINE FORM I OF IBRUTINIB

CROSS REFERENCE TO RELATED APPLICATIONS

This application claims priority under 35 U.S.C. §119(a) to Chinese Patent Application No. 201310616065.4, filed on Nov. 27, 2013, and Application No. 201410542609.1, filed on Oct. 14, 2014, both of which are herein incorporated by reference in their entireties.

FIELD OF THE INVENTION

This invention relates to a novel crystalline form of ibrutinib, and pharmaceutical compositions, methods of preparation, and method of uses thereof.

BACKGROUND OF THE INVENTION

Bruton's tyrosine kinase (BTK) is a key signaling enzyme expressed in all hematopoietic cell types except T lymphocytes and natural killer cells and a key regulator of B-cell development, activation, signaling, and survival. It plays an essential role in the B-cell signaling pathway linking cell surface B-cell receptor (BCR) stimulation to downstream intracellular responses. Thus, among others, BTK contributes to the proliferation and survival of B cells, which are the white blood cells that turn malignant in mantle cell lymphoma.

Ibrutinib is the first BTK inhibitor approved by the U.S. Food and Drug Administration for the treatment of mantle cell lymphoma. Ibrutinib has a structure of formula (I), with a chemical name as 1-[(3R)-3-[4-amino-3-(4-phenoxyphenyl)-1H-pyrazolo [3,4-d]pyrimidin-1-yl]piperidin-1-yl] prop-2-en-1-one.

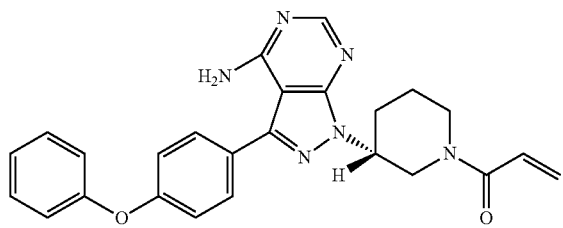

(I)

Polymorphism of ibrutinib has been reported in WO2013184572, which discloses six crystalline forms of ibrutinib, including 3 anhydrous forms and 3 solvates (i.e., methyl isobutyl ketone solvate, toluene solvate, and methanol solvate, respectively), obtained through screening a large number of solvent systems, including their mixtures. The two better-studied unsolvated forms of ibrutinib were reported to have low solubility (Form A 0.013 mg/mL at pH=8 and Form B 0.0096 mg/mL at pH=7.42). Moreover, the solvate forms are not suitable for use directly in dosage forms.

Therefore, new crystalline forms of ibrutinib, in particular stable unsolvated polymorphs with superior pharmacological properties remain a great need.

SUMMARY OF THE INVENTION

The present invention provides a surprisingly discovered new crystalline form of ibrutinib having desired pharmacological properties, for example, higher stability and solubility and low hygroscopicity, which make it more suitable for use in dosage forms to achieve desired bioavailability and therapeutic effects. The crystalline form can also be prepared using simple process in a low cost.

In one aspect, the present invention provides a crystalline form of ibrutinib, designated as Form I.

In another aspect, the present invention provides process for preparation of ibrutinib Form I.

In another aspect, the present invention provides pharmaceutical compositions comprising the crystalline Form I of ibrutinib and a pharmaceutically acceptable carrier.

In another aspect, the present invention provides a method of using crystalline Form I of ibrutinib in the manufacture of a medicament for treatment of a disease or disorder in connection with BTK activities.

In another aspect, the present invention provides a method of treating a disease or disorder in connection with BTK activities, comprising administering to a subject in need thereof a pharmaceutical composition comprising crystalline Form I of ibrutinib.

Other aspects and embodiments of the present invention will be further illustrated in the following description and examples.

DETAILED DESCRIPTION OF THE INVENTION

The present invention provides a new crystalline form of ibrutinib, which has a higher solubility under physiological conditions than crystalline Form A of WO2013184572, and thus provides various advantages, such as enhanced bioavailability and reduced drug loading. The new crystalline form is physically and chemically stable, is not hygroscopic and does not become deliquescent at a high humidity, and is therefore convenient for long-term storage. Moreover, the new crystalline form can be prepared using a simple process in a low cost, which is also highly valuable for further optimization and development of the drug in the future.

In one aspect, the present invention provides a crystalline form of ibrutinib, designated as Form I.

In one embodiment, the crystalline Form I is characterized by an X-ray powder diffraction pattern comprising the following 2θ values measured using CuKα radiation: 5.2°±0.2°, 17.6°±0.2°, and 22.1°±0.2°.

In another embodiment, the crystalline Form I is characterized by an X-ray powder diffraction pattern further comprising the following 2θ values measured using CuKα radiation: 19.3°±0.2°, 20.8°±0.2°, and 22.4°±0.2°.

In another embodiment, the crystalline Form I is characterized by an X-ray powder diffraction pattern further comprising the following 2θ values measured using CuKα radiation: 16.2°±0.2°, 18.1°±0.2°, 18.9°±0.2°, and 23.0°±0.2°.

Figure 1:
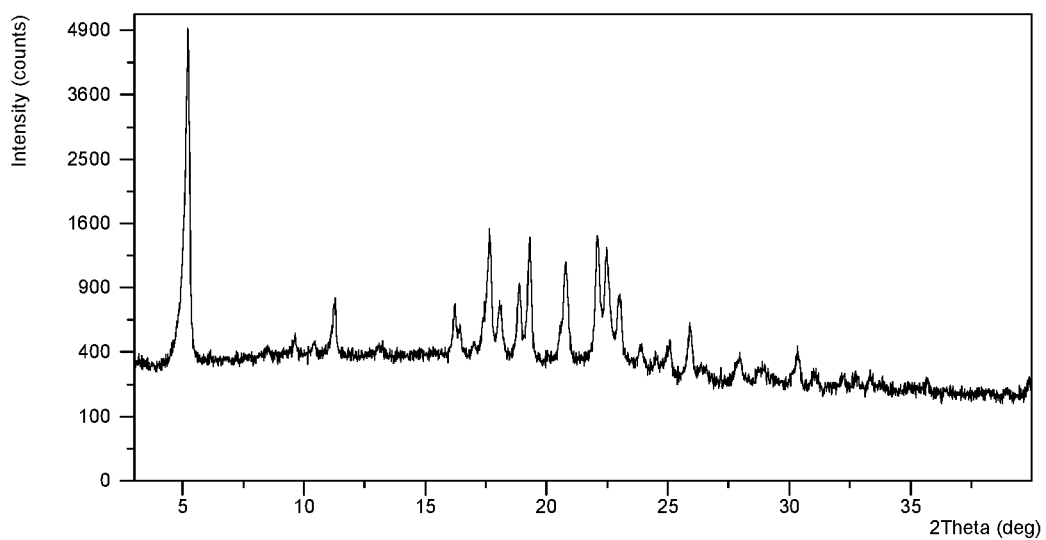
FIG. 1 shows a representative X-ray powder diffraction (XRPD) pattern of crystalline Form I.

The crystalline Form I has an X-ray powder diffraction pattern substantially as shown in FIG. 1.

Figure 2:
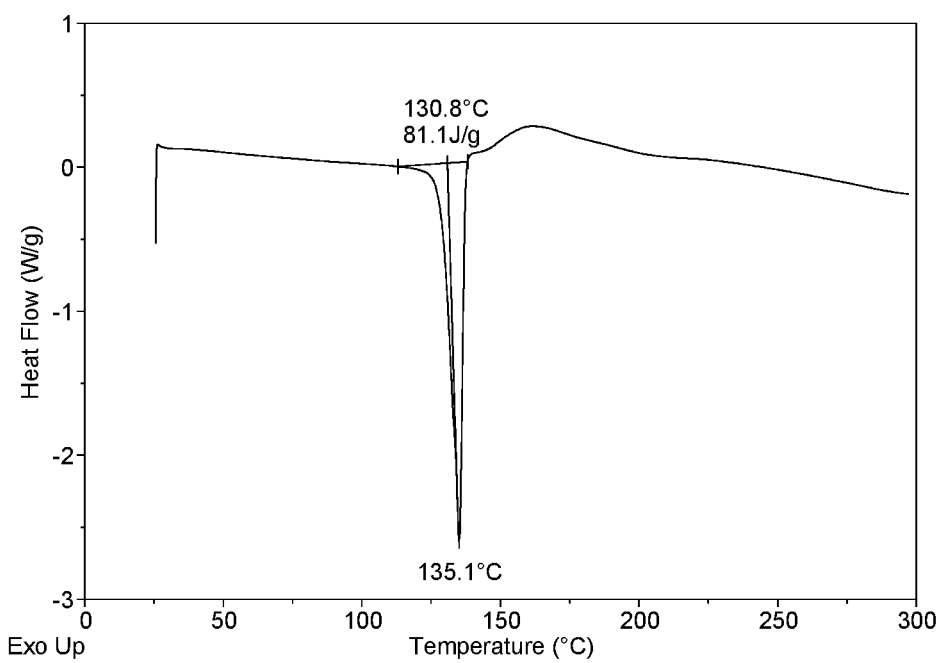
FIG. 2 shows a representative differential scanning calorimetric (DSC) thermogram of crystalline Form I.

The crystalline Form I has a differential scanning calorimetric thermogram substantially as shown in FIG. 2, which exhibits an endothermic peak at about 135.1° C.

Figure 3:
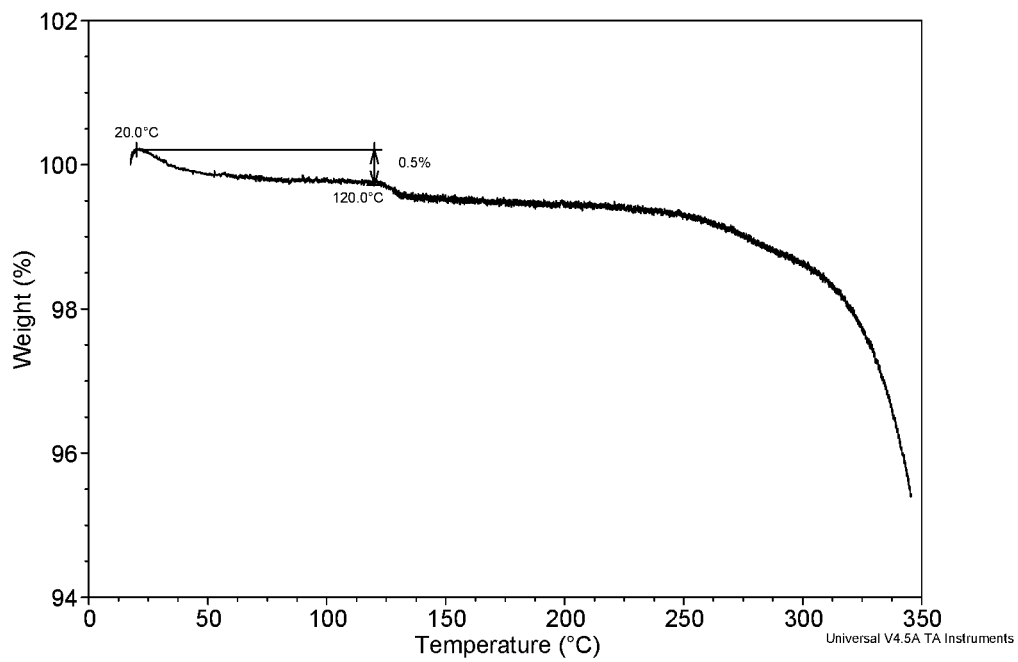
FIG. 3 shows a representative thermal gravimetric analysis (TGA) thermogram of crystalline Form I.

The crystalline Form I has a thermal gravimetric analysis thermogram substantially as shown in FIG. 3, which exhibits about 0.5% weight loss up to 120° C., suggesting that the crystalline form is substantially unsolvated and anhydrous.

In another aspect, the present invention provides a process for preparation of ibrutinib Form I, comprising: dissolving ibrutinib in alcohol, ether, or ketone, or a mixture or alcohol, ether, or ketone with an alkane; and crystallizing said Form I from the solution, either by equilibration under ambient conditions or by controlled cooling.

In some embodiments, said dissolving is conducted in a mixed solvent system comprising an alcohol and an alkane.

In some embodiments, said mixed solvent system comprises 2-propanol and n-heptane.

In another aspect, the present invention provides solid pharmaceutical compositions comprising ibrutinib Form I. Form I of ibrutinib together with one or more pharmaceutically acceptable excipients of the present invention may be further formulated as: solid oral dosage forms such as, but not limited to, powders, granules, pellets, tablets, and capsules; liquid oral dosage forms such as, but not limited to, syrups, suspensions, dispersions, and emulsions; and injectable preparations such as, but not limited to, solutions, dispersions, and freeze dried compositions.

In another aspect, the present invention provides a method for treating cancer in a mammal, comprising administering a therapeutically effective amount of ibrutinib Form I. In some embodiments, the cancer is a B cell malignancy. In some embodiments, the cancer is a B cell malignancy selected from chronic lymphocytic leukemia (CLL)/small lymphocytic lymphoma (SLL), mantle cell lymphoma (MCL), diffuse large B Cell lymphoma (DLBCL), and multiple myeloma.

In another aspect, the present invention provides use of ibrutinib Form I in the manufacture of a medicament for the treatment of a disease or disorder related to BTK activities. In an embodiment, the disease or disorder is a B cell malignancy selected from the group consisting of chronic lymphocytic leukemia (CLL)/small lymphocytic lymphoma (SLL), mantle cell lymphoma (MCL), diffuse large B Cell lymphoma (DLBCL), and multiple myeloma.

The following non-limiting examples further illustrate certain aspects of the present invention.

EXAMPLES

X-Ray Powder Diffraction (XRPD)

Analytical Instrument: Panalytical Empyrean. The X-ray powder diffraction was conducted by mounting a sample of the crystalline material on a Si single crystal low-background holder and spreading out the sample into a thin layer with the aid of a microscope slide. The 2θ position was calibrated against Panalytical 640 Si powder standard. The sample irradiated with X-rays generated by a copper long-fine focus tube operated at 45 kV and 40 mA with a wavelength of Kα1=1.540589 angstroms and Kα2=1.544426 angstroms (Kα1/Kα2 intensity ratio is 0.50). The collimated X-ray source was passed through a programmed divergence slit set at 10 mm and the reflected radiation directed through a 5.5 mm anti-scatter slit. The sample was exposed for 16.3 seconds per 0.013° 2-theta increment (continuous scan mode) over the range 3 degrees to 40 degrees 2-theta in theta-theta mode. The running time was 3 minutes and 57 seconds. The instrument was equipped with a RTMS detector (X'Celerator). Control and data capture was by means of a Dell Optiplex 780 XP operating with data collector software.

Persons skilled in the art of X-ray powder diffraction will realize that the relative intensity of peaks can be affected by, for example, grains above 30 microns in size and non-unitary aspect ratios that may affect analysis of samples. The skilled person will also realize that the position of reflections can be affected by the precise height at which the sample sits in the diffractometer and the zero calibration of the diffractometer. The surface planarity of the sample may also have a small effect. Hence the diffraction pattern data presented are not to be taken as absolute values.

Differential Scanning Calorimetry (DSC)

Analytical Instrument: TA Instruments Q2000 DSC.

Heating rate: 10° C. per minute.

Purge gas: nitrogen

Thermal Gravimetric Analysis (TGA)

Analytical Instrument: TA Instruments Q5000 TGA.

Heating rate: 10° C. per minute.

Purge gas: nitrogen.

Dynamic Vapor Sorption (DVS)

Dynamic Vapor Sorption (DVS) was measured via a SMS (Surface Measurement Systems) DVS Intrinsic. The relative humidity at 25° C. were calibrated against deliquescence point of LiCl, Mg(NO$_3$)$_2$ and KCl. Typical Parameters for DVS test are listed below.

| Parameters for DVS test | |
|---|---|
| Parameters | Settings /Values |
| Temperature | 25° C. |
| Sample size | 10~20 mg |
| Gas and flow rate | N2, 200 mL/min |
| dm/dt | 0.002%/min |
| Min. dm/dt stability duration | 10 min |
| Max. equilibrium time | 180 min |
| RH range | 0% RH to 95% RH |
| RH step size | 10% RH from 0% RH to 90% RH |
| | 5% RH from 90% RH to 95% RH |

Example 1. Preparation of Ibrutinib Crystalline Form I

In 15 mL of 2-propanol/n-heptane (2:3, v/v) was dissolved 513 mg of ibrutinib. The solution was equilibrated under ambient conditions for 24 h, and Form I was obtained, which was analyzed by XRPD, DSC, and TGA. The XRPD pattern of Form I is displayed in FIG. 1. The XRPD data of Form I produced in this example are listed in Table 1.

The XRPD pattern of Form I obtained from this Example is displayed in FIG. 1, the DSC thermogram of Form I obtained from this Example is displayed in FIG. 2; and the TGA thermogram of Form I obtained from this Example is displayed in FIG. 3.

TABLE 1

| 2 theta | d spacing | intensity % |
| --- | --- | --- |
| 5.23 | 16.89 | 100.00 |
| 11.27 | 7.85 | 7.82 |
| 16.23 | 5.46 | 8.22 |
| 17.67 | 5.02 | 25.59 |
| 18.09 | 4.90 | 8.37 |
| 18.89 | 4.70 | 13.25 |
| 19.32 | 4.59 | 23.58 |
| 20.80 | 4.27 | 17.62 |
| 22.11 | 4.02 | 24.90 |
| 22.50 | 3.95 | 20.49 |
| 23.02 | 3.86 | 11.68 |
| 25.06 | 3.55 | 3.66 |
| 25.94 | 3.44 | 7.06 |
| 27.96 | 3.19 | 2.75 |
| 30.37 | 2.94 | 3.57 |

Example 2. Preparation of Ibrutinib Crystalline Form I

In 1.6 mL of 2-propanol/n-heptane (1:5, v/v) was dissolved 48.2 mg of ibrutinib to get a saturated solution of ibrutinib under 50° C. The solution was cooled from 50° C. to 5° C. at a cooling rate of 0.1° C./min, and Form I was produced. The XRPD data of Form I produced in this example are listed in Table 2.

TABLE 2

| 2 theta | d spacing | intensity % |
| --- | --- | --- |
| 5.15 | 17.16 | 57.06 |
| 8.43 | 10.49 | 5.45 |
| 9.56 | 9.25 | 7.08 |
| 11.20 | 7.90 | 15.39 |
| 13.06 | 6.78 | 1.74 |
| 16.15 | 5.49 | 35.51 |
| 16.36 | 5.42 | 19.08 |
| 16.94 | 5.23 | 7.01 |
| 17.31 | 5.12 | 17.28 |
| 17.57 | 5.05 | 28.02 |
| 17.96 | 4.93 | 27.91 |
| 18.03 | 4.92 | 34.36 |
| 18.82 | 4.72 | 31.86 |
| 19.25 | 4.61 | 66.12 |
| 20.73 | 4.28 | 35.16 |
| 22.03 | 4.04 | 100.00 |
| 22.40 | 3.97 | 26.54 |
| 22.94 | 3.88 | 42.42 |
| 23.84 | 3.73 | 11.05 |
| 24.46 | 3.64 | 3.60 |
| 25.00 | 3.56 | 12.43 |
| 25.84 | 3.45 | 13.98 |
| 26.27 | 3.39 | 3.22 |
| 27.80 | 3.21 | 4.80 |
| 28.43 | 3.14 | 1.75 |
| 28.87 | 3.09 | 9.22 |
| 29.37 | 3.04 | 2.72 |
| 30.28 | 2.95 | 7.21 |
| 30.97 | 2.89 | 9.78 |
| 32.14 | 2.78 | 4.45 |
| 32.76 | 2.73 | 5.35 |
| 33.27 | 2.69 | 1.69 |
| 33.83 | 2.65 | 4.33 |
| 35.30 | 2.54 | 1.30 |
| 35.63 | 2.52 | 2.31 |
| 36.49 | 2.46 | 1.39 |
| 38.93 | 2.31 | 1.48 |

Example 3. Preparation of Ibrutinib Crystalline Form I

In 0.5 mL of acetone was dissolved 12.7 mg of ibrutinib, followed by the slow addition of 2.0 mL of n-heptane. The suspension was stirred at a rate of 1000 rpm for one day, and Form I was produced. The XRPD data of Form I produced in this example are listed in Table 3.

TABLE 3

| 2 theta | d spacing | intensity % |
| --- | --- | --- |
| 5.22 | 16.94 | 100.00 |
| 7.02 | 12.59 | 2.89 |
| 8.50 | 10.41 | 5.28 |
| 9.63 | 9.18 | 7.07 |
| 10.42 | 8.49 | 3.05 |
| 11.25 | 7.86 | 15.50 |
| 13.10 | 6.76 | 1.63 |
| 16.21 | 5.47 | 30.87 |
| 16.42 | 5.40 | 15.63 |
| 17.00 | 5.22 | 5.53 |
| 17.35 | 5.11 | 11.19 |
| 17.64 | 5.03 | 31.15 |
| 18.07 | 4.91 | 22.18 |
| 18.87 | 4.70 | 29.94 |
| 19.29 | 4.60 | 53.00 |
| 20.54 | 4.32 | 8.00 |
| 20.77 | 4.28 | 28.83 |
| 22.08 | 4.03 | 58.55 |
| 22.46 | 3.96 | 24.62 |
| 23.01 | 3.87 | 23.53 |
| 23.90 | 3.72 | 6.55 |
| 24.53 | 3.63 | 3.39 |
| 25.06 | 3.55 | 7.48 |
| 25.89 | 3.44 | 11.71 |
| 27.96 | 3.19 | 4.60 |
| 28.94 | 3.09 | 4.30 |
| 30.34 | 2.95 | 5.67 |
| 31.02 | 2.88 | 4.58 |
| 32.18 | 2.78 | 1.93 |
| 32.80 | 2.73 | 2.82 |
| 33.87 | 2.65 | 1.92 |
| 35.68 | 2.52 | 1.48 |
| 36.55 | 2.46 | 0.94 |
| 37.93 | 2.37 | 0.46 |

Example 4. Kinetic Solubility Comparison Between Crystalline Form I of Ibrutinib and Crystalline Form a (WO2013184572A1)

Kinetic solubility of ibrutinib in crystalline Form I and in crystalline Form A (WO2013184572A1) in fed state simulated intestinal fluid (FeSSIF) and simulated gastric fluid (SGF) were measured using the following procedures:

1. Weigh approximately 30 mg of ibrutinib crystalline Form A or Form I into a tared 4-mL plastic vial and record the actual weight of the compound.

2. Add 3 mL of bio-relevant medium into each vial.

3. Cap the vials and keep all the suspension samples stirring at RT (room temperature) using a rolling incubator at a rate of 25 r/min.

4. Sample at 1 h, 4 h and 24 h respectively. About 0.6 mL aliquot of the suspension is transferred per time from solubility vial into a centrifuge filtration tube (pore size of 0.45 μm).

5. Centrifuge filtration tubes at a rate of 8500 rpm for 3 minutes at RT, collect 0.2 mL of supernatant for HPLC quantification determination and collect the rest of solution for pH measurement, and separate the solid for XRPD characterization.

The results displayed in Table 4 suggest crystalline Form I has higher solubility in comparison to crystalline Form A (WO2013184572A1).

TABLE 4

| Time | FeSSIF | | SGF | |
|---|---|---|---|---|
| point (h) | Form I | WO2013184572A1 Form A | Form I | WO2013184572A1 Form A |
| Solubility (mg/mL) 1 | 0.15 | 0.10 | 0.50 | 0.36 |
| 4 | 0.16 | 0.11 | 0.50 | 0.39 |
| 24 | 0.16 | 0.13 | 0.48 | 0.38 |

Example 5. Hygroscopicity Assessment of Form I

Figure 4:
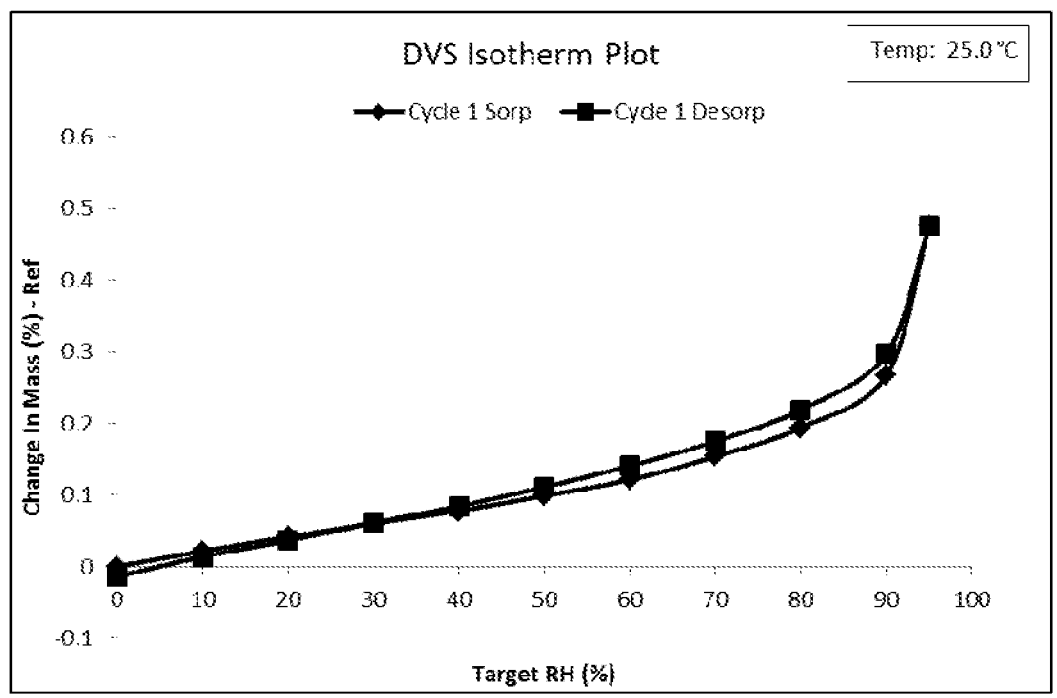
FIG. 4 shows a representative dynamic vapor sorption (DVS) isotherm plot of crystalline Form I.

Hygroscopicity of ibrutinib Form I was investigated using dynamic vapor sorption (DVS). The DVS isotherm plot of Form I displayed in FIG. 4 and the detailed data listed in Table 5 show that the sample has 0.19% water uptake under 80% RH, 25° C., suggesting Form I is non-hygroscopic.

TABLE 5

| Solid Form | Water uptake under 80% RH | Water uptake under 95% RH |
|---|---|---|
| Ibrutinib Form I | 0.19% | 0.48% |

Hygroscopicity criteria applied in this example refer to the standard in European pharmacopoeia:
  deliquescent: sufficient water is absorbed to form a liquid;
  very hygroscopic: increase in mass is equal to or greater than 15 percent;
  hygroscopic: increase in mass is less than 15 percent and equal to or greater than 2 percent;
  slightly hygroscopic: increase in mass is less than 2 percent and equal to or greater than 0.2 percent.

Example 6. Stability Assessment of Form I Under Stress Conditions

Figure 5:
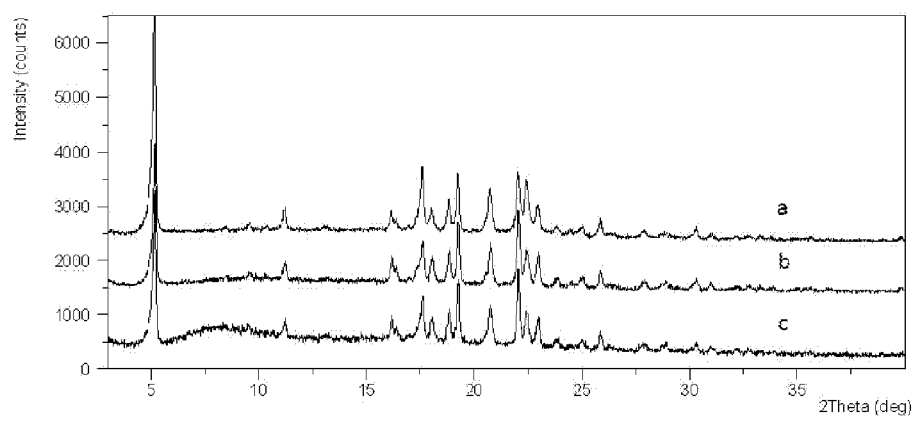
FIG. 5 shows the change in the XRPD pattern of Form I when stored at 25° C./60% RH for 180 days (FIG. 5b) and 40° C./75% RH for 180 days (FIG. 5c) as compared to the original Form I (FIG. 5a).

Two samples of ibrutinib Form I were stored under 25° C./60% RH and 40° C./75% RH, respectively, with dish open for 180 days. The chemical and physical stabilities of the samples were evaluated by high performance liquid chromatography (HPLC) and XRPD. The XRPD patterns of Form I under stress conditions are displayed in FIG. 5. The result of stability assessment tabulated in Table 6 indicates that Form I is physically and chemically stable under the stress conditions.

TABLE 6

| Initial Form | conditions | Storage time | Chemical purity | Final form |
|---|---|---|---|---|
| Form I (FIG. 5 a) | 25° C./60% RH | 180 days | 98.98% | Form I (FIG. 5 b) |
| Form I (FIG. 5 a) | 40° C./75% RH | 180 days | 98.98% | Form I (FIG. 5 c) |

The foregoing examples and description of the preferred embodiments should be taken as illustrating, rather than as limiting, the present invention as defined by the claims. As will be readily appreciated by a person skilled in the art, numerous variations and combinations of the features set forth above can be utilized without departing from the present invention as set forth in the claims. All such variations are intended to be included within the scope of the following claims. All references cited herein are incorporated by reference in their entireties.

What is claimed is:

1. A crystalline form of ibrutinib, designated as Form I, having an X-ray powder diffraction pattern comprising the following 2θ values measured using CuKα radiation: 5.2°±0.2°, 17.6°±0.2°, and 22.1°±0.2°.

2. The crystalline form of claim 1, wherein the X-ray powder diffraction pattern further comprises the following 2θ values measured using CuKα radiation: 19.3°±0.2°, 20.8°±0.2°, and 22.4°±0.2°.

3. The crystalline form of claim 1, wherein the X-ray powder diffraction pattern further comprises the following 2θ values measured using CuKα radiation: 16.2°±0.2°, 18.1°±0.2°, 18.9°±0.2°, and 23.0°±0.2°.

4. The crystalline form of claim 1, having an X-ray powder diffraction pattern substantially as depicted in FIG. 1.

5. The crystalline form of claim 1, having a differential scanning calorimetric thermogram substantially as depicted in FIG. 2.

6. The crystalline form of claim 1, having a thermal gravimetric analysis thermogram substantially as depicted in FIG. 3.

7. A process for the preparation of ibrutinib Form I, comprising: dissolving ibrutinib in a solvent system selected from the group consisting of alcohol having three or more carbon atoms, ether, ketone, a mixture of alcohol with alkane, a mixture of ether and alkane, and a mixture of ketone with alkane to form a solution; and crystallizing said Form I by cooling the solution under ambient conditions or in a controlled manner.

8. The process according to claim 7, wherein said solvent system is a mixture of an alcohol or ketone and an alkane.

9. The process according to claim 8, wherein said alcohol is a lower alcohol, and said alkane is a $C_4$-$C_{10}$ alkane.

10. The process according to claim 8, wherein the solvent system is a mixture of 2-propanol and n-heptane.

11. The process according to claim 8, wherein said ketone is a $C_3$-$C_6$ ketone, and said alkane is a $C_4$-$C_{10}$ alkane.

12. The process according to claim 8, wherein the solvent system is a mixture of acetone and n-heptane.

13. A pharmaceutical composition comprising crystalline Form I of ibrutinib and a pharmaceutically acceptable carrier, wherein said crystalline Form I has an X-ray powder diffraction pattern comprising the following 2θ values measured using CuKα radiation: 5.2°±0.2°, 17.6°±0.2°, and 22.1°±0.2°.

14. The pharmaceutical composition of claim 13, wherein the X-ray powder diffraction pattern of said crystalline Form I further comprises the following 2θ values measured using CuKα radiation: 19.3°±0.2°, 20.8°±0.2°, and 22.4°±0.2°.

15. The pharmaceutical composition of claim 13, wherein the X-ray powder diffraction pattern further comprises the following 2θ values measured using CuKα radiation: 16.2°±0.2°, 18.1°±0.2°, 18.9°±0.2°, and 23.0°±0.2°.

16. The pharmaceutical composition of claim 13, wherein said crystalline Form I has a melting point at about 135.1° C. as measured by differential scanning calorimetry (DSC).

17. The pharmaceutical composition of claim 13, wherein the X-ray powder diffraction pattern of said crystalline Form I has an X-ray powder diffraction pattern substantially as depicted in FIG. 1.

18. A method of treating or delaying the progression or onset of a disease or disorder in connection with activity of a Bruton's tyrosine kinase (BTK), comprising administering to a subject in need thereof a pharmaceutical composition comprising crystalline Form I of ibrutinib.

19. The method of claim 18, wherein said disease or disorder is a B cell malignancy selected from the group consisting of chronic lymphocytic leukemia (CLL)/small lymphocytic lymphoma (SLL), mantle cell lymphoma (MCL), diffuse large B Cell lymphoma (DLBCL), and multiple myeloma.

* * * * *